United States Patent [19]

Ito

[11] Patent Number: 4,753,734

[45] Date of Patent: Jun. 28, 1988

[54] ANGLE ROTOR COIL PLANET CENTRIFUGE FOR COUNTERCURRENT CHROMATOGRAPHY AND PARTICLE SEPARATION

[75] Inventor: Yoichiro Ito, Bethesda, Md.

[73] Assignee: The United States of America as represented by the Department of Health and Human Services, Washington, D.C.

[21] Appl. No.: 52,209

[22] Filed: May 19, 1987

Related U.S. Application Data

[63] Continuation-in-part of Ser. No. 823,115, Jan. 23, 1986, abandoned.

[51] Int. Cl.⁴ .............................................. B01D 15/08
[52] U.S. Cl. .................................. 210/657; 210/198.2
[58] Field of Search ...................... 210/635, 657, 198.2, 210/511, 781; 55/67, 386

[56] References Cited

U.S. PATENT DOCUMENTS

| | | |
|---|---|---|
| 3,775,309 | 11/1973 | Ito ........................ 210/635 |
| 3,856,669 | 12/1974 | Ito ........................ 210/657 |
| 3,994,805 | 11/1976 | Ito ........................ 210/657 |
| 4,324,661 | 4/1982 | Ito ........................ 210/635 |
| 4,414,108 | 11/1983 | Ito ........................ 210/198.2 |
| 4,430,216 | 2/1984 | Ito ........................ 210/198.2 |
| 4,532,039 | 7/1985 | Ito ........................ 210/198.2 |

Primary Examiner—Ernest G. Therkorn
Attorney, Agent, or Firm—Browdy and Neimark

[57] ABSTRACT

An apparatus for performing efficient and stable separation of one material from the other using countercurrent chromatography. The apparatus includes a column holder, which is inclined at an optimum angle between 0° and 90°, having a column wrapped thereabout. The configuration and orientation of the column may be varied depending on the properties of two-phase solvent system. A major feature is that the column holder rotates about its central longitudinal axis and the central vertical axis at the same angular velocity and in the same direction.

15 Claims, 3 Drawing Sheets

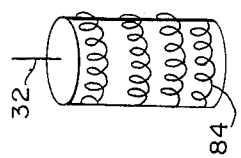
FIG. 7a
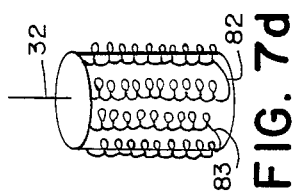
FIG. 7b
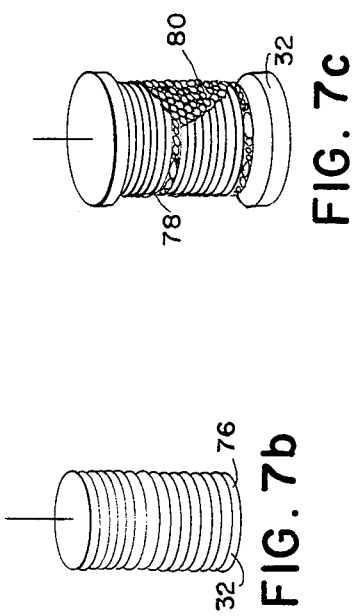
FIG. 7c
FIG. 7d
FIG. 7e
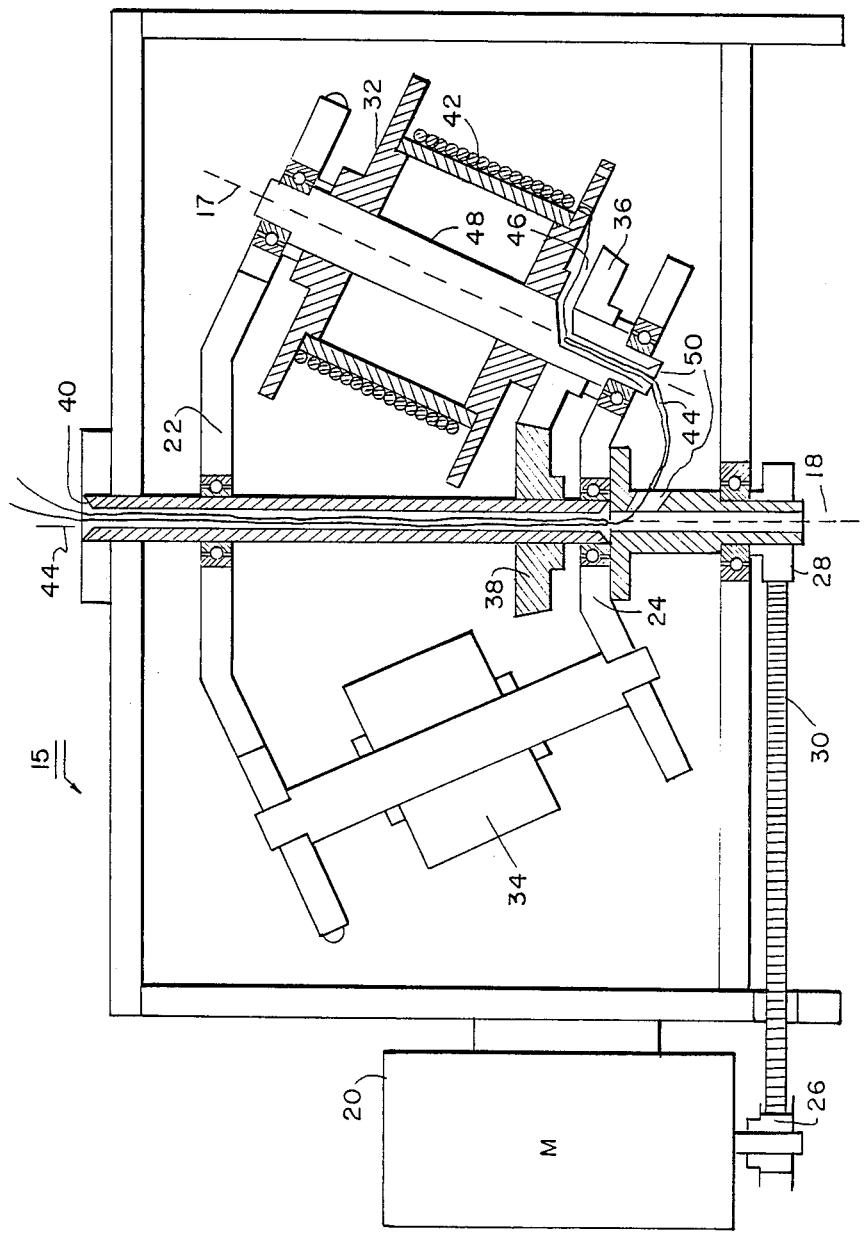
FIG. 6

4,753,734

ANGLE ROTOR COIL PLANET CENTRIFUGE FOR COUNTERCURRENT CHROMATOGRAPHY AND PARTICLE SEPARATION

This application is a continuation-in-part of application Ser. No. 823,115, filed Jan. 23, 1986, now abandoned.

FIELD OF INVENTION

The present invention relates to continuous countercurrent chromatography and particle separation, and, more particularly, to an improved coil planet centrifuge apparatus for performing countercurrent chromatography and separations of polar compounds such as peptides and proteins and the like.

BACKGROUND OF THE INVENTION

In the past, various types of the rotary seal-free flow-through coil planet centrifuge devices have been developed, each having a specific advantages for performing particular types of separations. In most of these rotary seal-free flow-through coil planet centrifuge systems, a coiled helical column rotates around the central longitudinal axis of its column holder while simultaneously revolving around a second longitudinal axis i.e., the central axis of the centrifuge, parallel with or perpendicular to the central longitudinal axis. Depending on the relative direction of the rotation about the two axes with respect to one another, different results occur. For example, U.S. Pat. No. 3,755,309 discloses a system that produces exteremely vigorous and even mixing of the column contents, which is particularly suitable for analytical separations with a narrow-bore tubing. U.S. Pat. No. 3,856,669, discloses a horizontal type of coil planet centrifuge, called an elution centrifuge, that produces a stable centrifugal force field which retains viscous low interfacial tension polymer phase systems in the column for performing separations of macromolecules and cell particles.

Inverted orientations of the column holder described in U.S. Pat. No. 4,430,216, produce a unique heterogeneous centrifugal force field that results in a mixing zone in the helical column near the central axis of the centrifuge and a settling zone in the remote portion of the column. This system has been applied to countercurrent chromatography with a high peak resolution, due to the large volume of the stationary phase retained in the column. The system, however, has difficulty with hydrophilic solvent systems such as butanol/acetic acid/water (4:1:5), sec.-butanol/water and aqueous-aqueous polymer phase systems that have a tendency to emulsify. Butanol systems are extremely useful for separation of polar compounds such as peptides and small proteins, while polymer phase systems are ideal for partitioning large proteins and cell particles.

U.S. Pat. No. 3,994,805 discloses a centrifuge which revolves a helical column, at an inclined angle from the vertical, around the central axis of the centrifuge and yet maintains the column in a fixed orientation while it revolves. This centrifuge provides a force field strength between that of the centrifuges described in U.S. Pat. Nos. 3,856,669 and 3,775,309 and causes intermediate partitioning efficiency and stability.

SUMMARY OF THE INVENTION

It is, accordingly, an object of the present invention to obviate the deficiencies of the prior art, such as those indicated above.

It is a further object to provide for improved continuous countercurrent chromatography and particle separation.

It is yet a further object to provide an improved countercurrent chromatographic device with high separation efficiency in a short time.

It is yet another object of the present invention to provide an improved countercurrent chromatographic system with a highly stable centrifugal field to retain a polymer phase system.

The present invention accomplishes the above object and others by optimizing the holder angle, column configuration and orientation on the holder according to the physical properties of the two-phase solvent system.

BRIEF DESCRIPTION OF DRAWINGS

Further objects and advantages of the invention will become apparent from the following description and from the accompanying drawings, wherein:

FIG. 6 is a diagram of preferred embodiment.

FIG. 7 shows various separation tubing arrangements on the column holder.

DETAILED DESCRIPTION OF THE INVENTION

Figure 1:
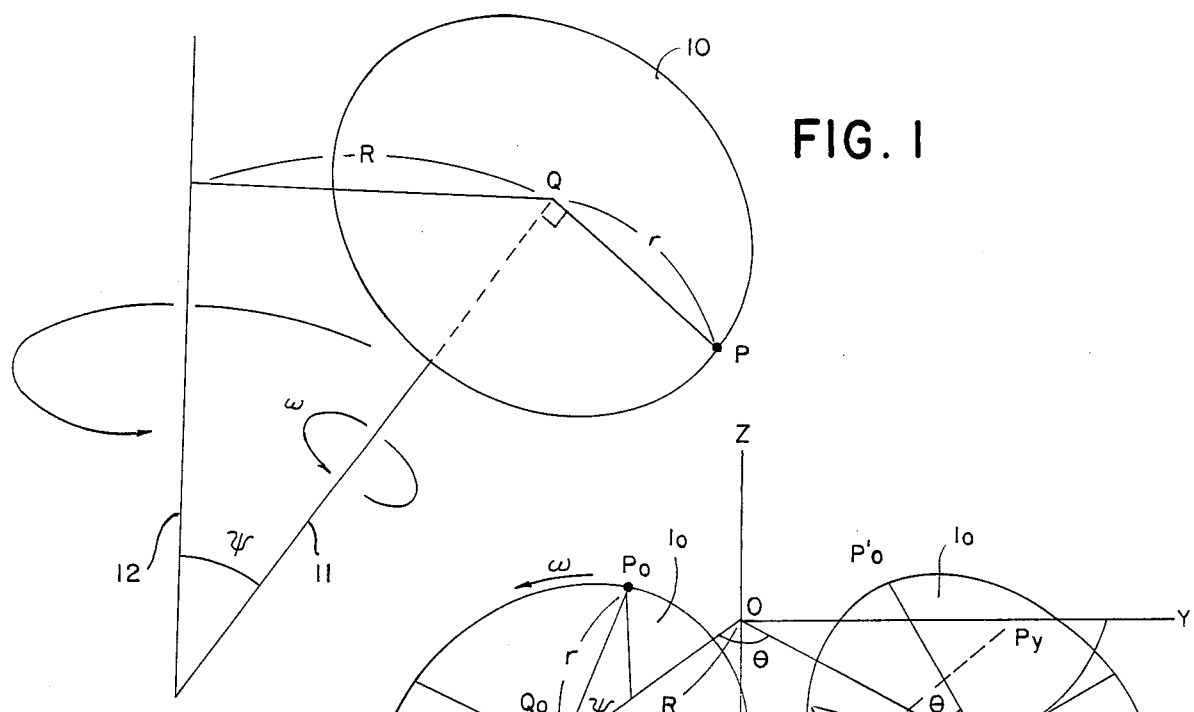
FIG. 1 shows a discoid body under a synchronous planetary motion.

FIG. 1 shows a discoid body 10, with radius r, its axis 11 being held at angle $\Psi$ from the central axis 12 of the stationary frame. The discoid body 10 undergoes a synchronous planetary motion in such a way that it revolves around the central axis 12 at an angular velocity with a revolutional axis R, and simultaneously rotates about its own axis at the same angular velocity. Point P is an arbitrary point on the periphery of discoid body 10.

Figure 2:
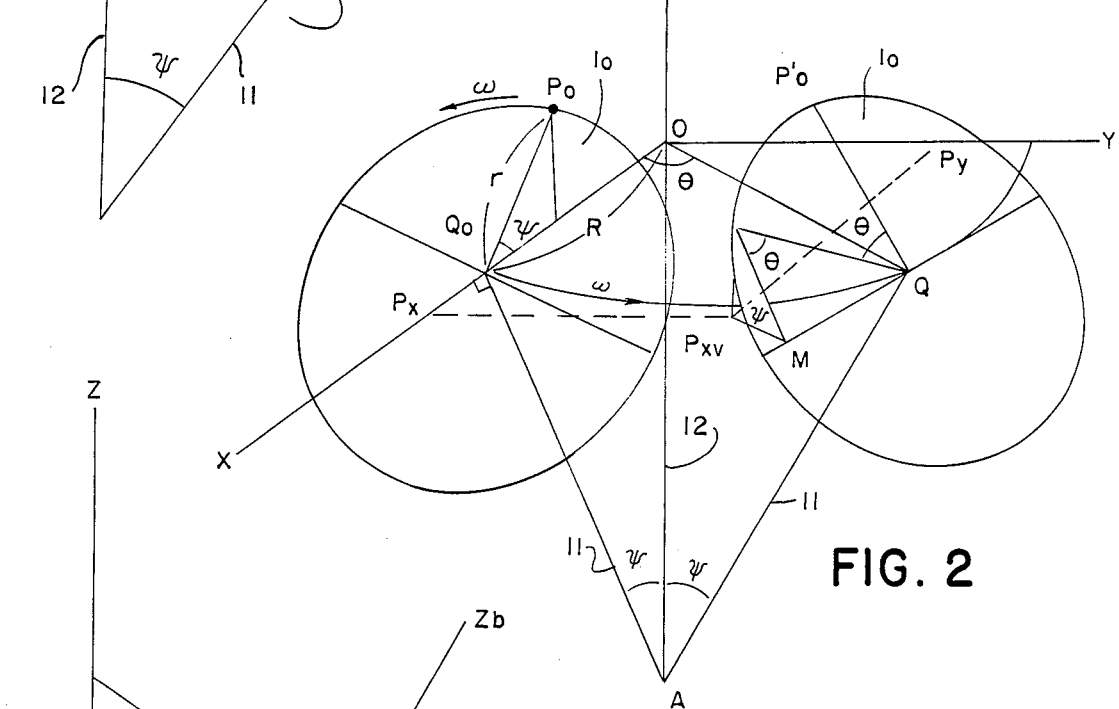
FIG. 2 shows a Cartesian coordinate system where the center of the discoid body locates at point $Q_o$ (R, O, O).

FIG. 2 shows an x, y, z coordinate system where the center of the discoid body 10 locates at point $Q_o$ (R, O, O) and the arbitrary point P at $P_o$ (R-rcos $\Psi$, O, rsin $\Psi$). The center of the discoid body circles around point O in the x+y plane and at time t moves an angle $\theta = \omega t$ to reach point (Rcos $\theta$, Rsin $\theta$, O). Then, the location of the arbitrary point on the discoid body 10 is expressed by P(x, y, z) according to the following equations:

$$x = R \cos \theta + r[1-(1+\cos \Psi) \cos^2 \theta] \qquad 1$$

$$y = R \sin \theta - r(1+\cos \Psi) \sin \theta \cos \theta \qquad 2$$

$$z = r \sin \Psi \cos \theta \qquad 3$$

where R is the distance OQ; r, the distance QP; and $\Psi$, the angle formed between z-axis and the body axis, QA.

The acceleration, $a$, produced by the planetary motion is then computed from the second derivatives of the above equations as $$a_x = d^2x/dt^2 = -R\omega^2[\cos\theta - 2\beta(1+\cos\Psi)\cos 2\theta] \quad (4)$$

$$a_y = d^2y/dt^2 = -R\omega^2[\sin\theta - 2\beta(1+\cos\Psi)\sin 2\theta] \quad (5)$$

$$a_z = d^2z/dt^2 = -r\omega^2 \sin\Psi \cos\theta \quad (6)$$

$$a_z = d^2z/dt^2 = -r\omega^2 \sin\Psi \cos\theta \quad (6)$$

where $\beta = r/R$ and $R \neq 0$. Using equations (4–6), the (x, y, z) components of the acceleration vector can be computed and displayed each separately or in a combined form in the (x, y, z) coordinate system of the stationary reference frame.

Figure 3:
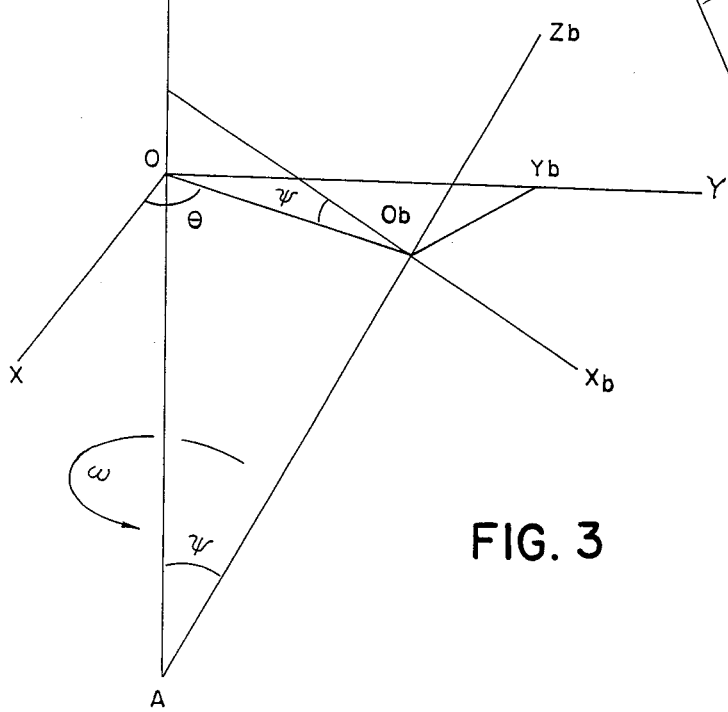
FIG. 3 illustrates the relationship between the original coordinate system of FIG. 2 and $(x_b, y_b, z_b)$ coordinate system, referred to as body coordinate system.

However, the effects of the acceleration on the subjects moving with the discoid body 10 can be more effectively visualized if the acceleration is expressed with respect to the revolving body frame. FIG. 3 shows the relationship between the original (x, y, z) coordinate system and the $x_b$, $y_b$, $z_b$ body coordinate system in which the $z_b$ axis coincides with the axis of the discoid body 10. The ($x_b$, $y_b$, $z_b$) coordinate system revolves around the z axis of the original coordinate system in such a way that the radially directed $x_b$ axis forms angle $\Psi$ against the $x+y$ plane while the $y_b$ axis is always confined in the same plane. Consequently, the discoid body 10 coaxially rotates around the $z_b$ axis at angular velocity $\omega$ in the $x_b + y_b$ plane.

Transformation of the acceleration from the original (x, y, z) coordinate system to the ($x_b$, $y_b$, $z_b$) body coordinate system can be performed by the following equations:

$$a_{\hat{x}b} = (a_x \cos\theta + a_y \sin\theta)\cos\Psi - a_z \sin 105 \quad (7)$$

$$a_{\hat{y}b} = -a_x \sin\theta + a_y \cos\theta \quad (8)$$

$$a_{\hat{z}b} = (a_x \cos\theta + a_y \sin\theta)\sin\Psi + a_z \cos\Psi \quad (9)$$

which become $$a_{\hat{x}b} = -R\omega^2[\cos\Psi - \beta(1+\cos\Psi)23 \cos\theta] \quad (10)$$

$$a_{\hat{y}b} = R\omega^2(1+\cos\Psi)2\beta \sin\theta = 2r\omega^2(1+\cos\Psi) \sin\theta \quad (11)$$

$$a_{\hat{z}b} = -R\omega^2 \sin\Psi[1 - \beta(2+\cos\Psi)\cos\theta] \quad (12)$$

For convenience of the diagrammatical expression of acceleration vectors, the first two components, $a_{\hat{x}b}$ and $a_{\hat{y}b}$, in the $x_b + y_b$ plane may be combined into a single vector, $a_{\hat{x}b+\hat{y}b}$. The magnitude of the vector, $|a_{\hat{x}b-\hat{y}b}|$ and the angle $\alpha$ formed to the $x_b$ axis are given in the following formulae:

$$|a_{\hat{x}b+\hat{y}b}| = (a_{\hat{x}b}^2 + a_{\hat{y}b}^2)^{\frac{1}{2}} \quad (13)$$

$$\gamma = \tan^{-1}(a_{\hat{y}b}/a_{\hat{x}b}), \text{ if } a_{\hat{x}b} > 0 \quad (14)$$

$$\gamma = \pi + \tan^{-1}(a_{\hat{y}b}/a_{\hat{x}b}), \text{ if } a_{\hat{x}b} < 0 \quad (15)$$

$$\gamma = \pm \frac{1}{2}\pi \text{ for } a_{\hat{y}b} > < 0, \text{ if } a_{\hat{x}b} = 0 \quad (16)$$

FIG. 4 shows examples of column holder orientations referred to earlier for reasons explained hereafter. FIGS. 4a–e are examples of column holder orientations referred to in the U.S. Pat. Nos. 3,755,309 (Type I), 3,994,805 (Type IL), 3,856,669 (Type J), the present invention (Type J-L), and 4,430,216 (Type J) respectively. Notice the direction of planetary motions 1, 2 and the position of separation tubing 3 of FIG. 4a–e with respect to axis 4.

Figure 4A:
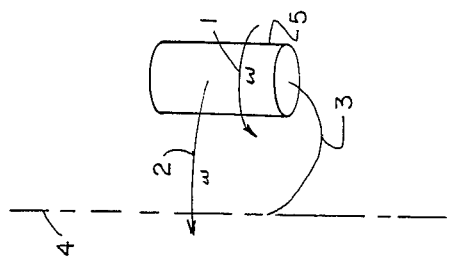
FIGS. 4a-e illustrate examples of different arrangements for the column holder and tubing inlet-outlet in a countercurrent chromatography column.
Figure 4B:
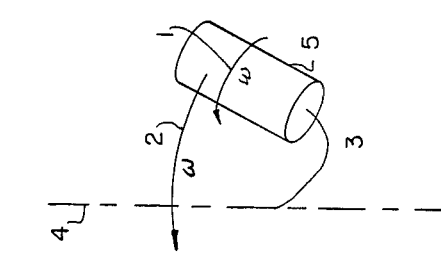
Figure 4C:
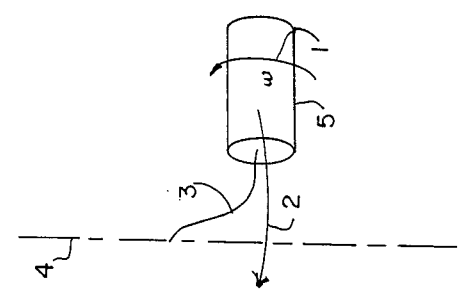
Figure 4D:
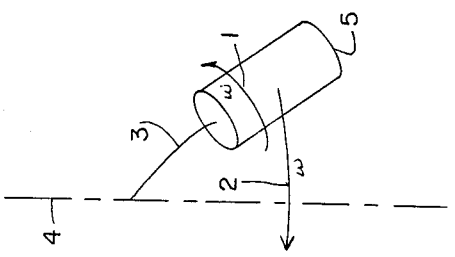
Figure 4E:
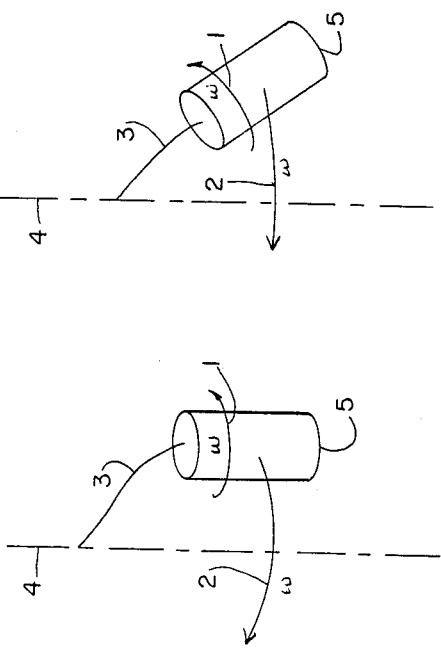
Figure 5A:
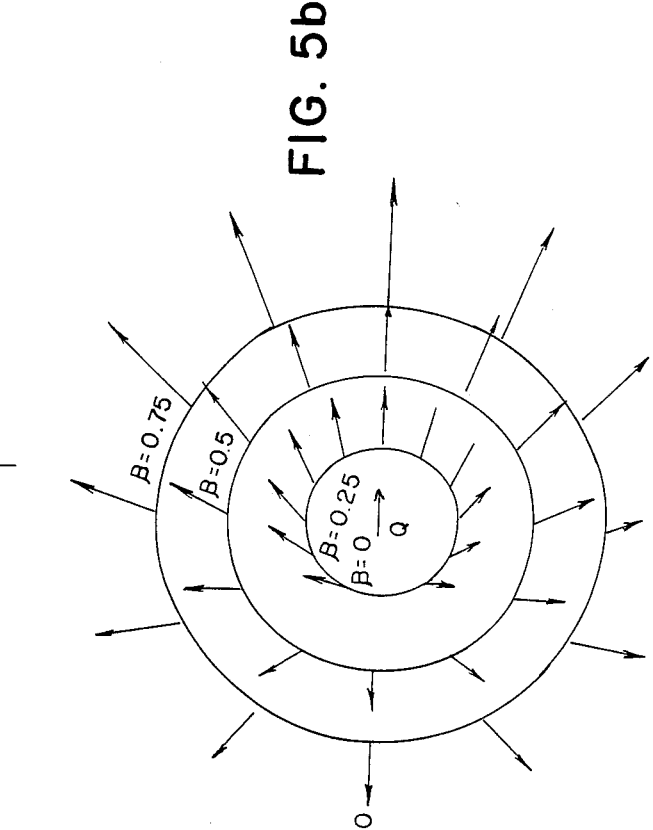
FIG. 5 shows the centrifugal force field produced by column holders of the types illustrated in FIGS. 4a through 4e.
Figure 5B:
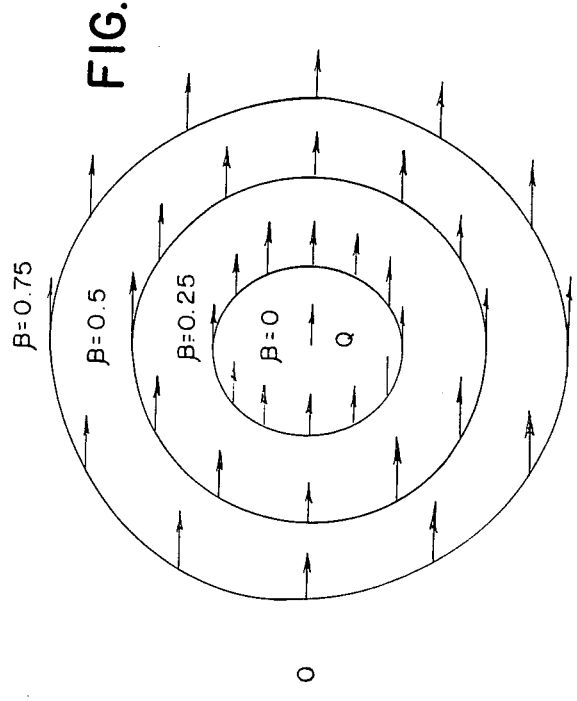

The centrifugal force fields momentarily produced by the planetary motion apparatus of FIG. 4a through FIG. 4e are illustrated in FIG. 5. Multiple concentric circles drawn in each diagram indicate the location of a point, P (FIG. 1), on the column holder 5 expressed by parameter $\beta = r/R$ where r represents the distance between P and $O_b$, and R represents the distance between $O_b$ and O.

The first column (left) recites each type of synchronous planetary motion. The second column gives the angle $\Psi$ characteristic of each type of synchronous planetary motion. In the two hybrid types, Type I-L and Type J-L, $\Psi$ is chosen at 135° and 45°, respectively, to facilitate comparative studies.

The third column in FIG. 5 illustrates orientation and planetary motion of the discoid body. It also indicates orientation of the $x_b$-$y_b$-$z_b$ body coordinate system, which serves as a reference frame for the force distribution diagram shown in the next column. The orientation of the $x_b$-$y_b$-$z_b$ body coordinate system is selected in such a way that the $z_b$ force component acting upward from the discoid body is always indicated as an ascending column in the force distribution diagram, except for the transitional angle of $=90°$ where the $z_b$ force component acting radially from the center of revolution toward the periphery (right) is expressed as the ascending column. Accordingly, the orientation of the reference frame is corrected by rotating the $x_b$-$y_b$-$z_b$ coordinate frame around the $y_b$-axis by 180° for $\Psi > 90°$. This transposition also causes conversion of the $+/-$ signs for the $x_b$ force component to normalize the direction of the $x_b$-$y_b$ force vector expressed as an arrow in the force distribution diagram.

In the fourth and the final column in FIG. 5 (right), the distribution of the centrifugal force vectors (at centrifuge speeds at or above those critical for CCC) is displayed for various $\Psi$ values in the order from 180° (top) to 0° (bottom) using the reference body coordinate frame indicated in the third column. In order to facilitate comparison, the length of the arrows and the columns which represent the magnitude of the force vector is normalized on the basis of the unit ($R\omega^2$) used in the first diagram ($\Psi = 180°$) so that the lengths of vectors drawn in these diagrams accurately represent the relative magnitude of the force generated by the respective planetary motion at the same revolutional radius (R) and angular velocity ($\omega$).

Observation of the force distribution diagrams from the top through to the bottom reveals successive changes in the distribution patterns of the first force component (arrows), while distribution of the continuity between $\Psi = 135°$ and 90° due to the transposition of the $x_b$-$y_b$-$z_b$ reference frame as described earlier. At $\Psi = 180°$, the diagram shows homogeneous two-dimensional distribution of the centrifugal force vectors, each component measuring a unit length and acting in the same direction parallel to the radius of revolution. At $\Psi = 135°$, the force distribution becomes three-dimensional: the first component (arrow) shows somewhat diverged distribution with slight decrease in magnitude, while the second component (column) acts strongly downward on the left and slightly upward on the right.

When Ψ reaches the transitional angle of 90°, the first force component (arrow) forms symmetrical distribution always acting outwardly from the circle, while the second force component (column) acts very strongly upwrd (or toward the periphery along the radius of revolution) on the right. Here, it is interesting to note that the second force component also acts downward on the left, indicating that the centrifugal force is momentarily directed toward the center of revolution at the very top of the discoid body. This strange phenomenon, which as been reported elsewhere, is explained on the basis of the Coriolis force produced by the planetary motion. As Ψ is further decreased to 45°, the first force component (arrow) remarkably gains strength, especially on the right, while the second component (column) maintains the similar profile. Finally, at Ψ=0°, the distribution of the force vectors returns to the two-dimensional pattern as in the first diagram (Ψ=180°), but it consists of a complex arrangement of force vectors diverging from each circle with a great enhancement of the magnitude, especially at the remote location from the center of the discoid body.

Comparison between the two extreme types of synchronous planetary motion, Type I and Type J, reveals a remarkable difference in both the distribution patterns and magnitude of the centrigual force vectors under the same revolutional speed and radius.

The centrifugal force field of the FIG. 4a (Type I) planetary motion shows homogeneous distribution of the vectors regardless of the location of the point on the column holder. The centrifugal force field of the FIG. 4e (Type J) planetary motion exhibits an extremely complex heterogeneous field which varies in both magnitude and direction of the force vector according to the location of point P on the column holder. The apparatus of FIG. 4c (Type L) planetary motion produces a most stable force field with a strong force vector always directing along the axis of the column holder while a Coriolis force is rotating around the column holder axis. The tilted types (FIGS. 4b and d) produce intermediate patterns of the force fields and the stability of the fields depend on the angle formed between the holder axis and the centrifuge axis. The present invention uses the tilted type of FIG. 4d, which provides an intermediate force field between those of FIG. 4c (Type L) and FIG. 4e (Type J).

The above difference is clearly manifested in the hydrodynamic effects on the two immisicible solvent phases in the coiled column. As briefly mentioned earlier, the Type I planetary motion produces the basic hydrodynamic equilibrium where the two solvent phases are evenly distributed in the coiled column from the head toward the tail, while any excess of either phase remains at the tail. This hydrodynamic distribution of the two solvent phases can be utilized for performing CCC by introducing the mobile phase through the head of the coiled column. However, in this mode of elution the stationary phase volume retained in the column is substantially less than 50% of the total column capacity. On the other hand, the Type J planetary motion distributes the two solvent phases unilaterally in the rotating coil (coaxially mounted on the holder), where one phase entirely occupies the head side and the other phase the tail side. As previously described, this unilateral hydrodynamic distribution is capable of retaining a large volume of the stationary phase in the column and is considered to be ideal for performing CCC. Under a proper elution mode and flow-rate of the mobile phase, the retention of the stationary phase often exceeds 80% of the total column capacity. Hydrodynamic motion of the two solvent phases produced by this type of planetary motion has been observed under stroboscopic illumination. Experiments have revealed two distinct zones in each turn of the spiral column, a mixing zone of about a quarter turn located near the center of the centrifuge and a settling zone showing a clear interface of the two phases in the rest of the column. The high-partition efficiency characteristic of high-speed CCC may be largely attributed to this local mixing unique to the Type J synchronous planetary motion.

The asymmetrical distribution of strong radial force for components for Type JL and Type J is considered to be the cause for the unilateral hydrodynamic distribution of the two solvent phases in the rotating column. The second force component acting along the $Z_b$-axis (columns) in Type J–L is also considered beneficial for introducing efficient mixing of the two solvent phases or improving the retention of the stationary phase depending on the configuration of the coiled column on the rotating holder.

In general, a slight inclination of the column holder from the vertical is sufficient to bring about a substantial force component directed along and parallel to the column holder axis and result in significantly enhanced mixing and/or stationary phase retention compared with Type J planetary motion. On the other hand, for essentially asymmetrical radial force vectors to arise so that substantial unilateral hydrodynamic equilibrium may be established, the angle of column holder tilting from the axis of revolution must be noticeably less than 90°. For example, the axis of the column holder should preferably be tilted from 1° to 85° from the axis of revolution. It should be understood that, although the term "vertical axis" as used herein is synonomous with the axis of revolution, regardless of whether that axis is actually oriented vertically in relation to the surround environment.

FIG. 6 shows an example of a centrifuge 15 having a 25 degree angle between the holder axis 17 and central axis 18 of centrifuge 15. Motor 20 drives the rotary frame through a pair of toothed pulleys 26, 28 and a toothed belt 30. The rotary frame consists of a pair of plates 22, 24 bridge with links (not shown) and holds a column holder 32 and a counterweight 34 in the symmetrical position. The column holder 32 is equipped with a planetary angle gear 36 (12.5 degree angle) which is coupled with an identical sun gear 38 mounted around the central stationary pipe 40. This gear arrangement produces a synchronous planetary motion of the holder 32 in such a way that the holder 32 rotates about its own axis and simultaneously revolves around the central axis of the centrifuge 40 at the same angular velocity and in the same direction. The column 42 is made by winding a piece of tubing around the coil holder 32. The flow tubes 44 are first passed through the center hole 46 of the holder shaft 48 and led through the side hole 50 of the coupling pipe to enter the opening of central stationary pipe 40. These tubes may be lubricated with silicone grease and protected with a piece of plastic sheath (not shown) to prevent direct contact with metal parts.

FIGS. 7a–e show various column winding arrangements. In FIG. 7a a piece of tubing 70 is placed parallel to holder 32 axis 74. Adjacent parallel portions 70 are connected by a perpendicular end portion 71. In FIG. 7b the tubing 76 is coaxially wound around holder 32 making multiple turns. A long piece of tubing 78 can be compactly accommodate on holder 32 by forming multiple layers 80 of the coil as shown in FIG. 7c. In FIGS. 7d and 7e, the tubing 82, 84 respectively is first wound around a long flexible core which is in turn arranged around holder 32 as illustrated. In other words, the tubing is helically coiled. In FIG. 7d the multiple coil units are arranged parallel, adjacent parallel portion being joined by perpendicular end portions 83, to the holder axis, and in FIG. 7e the coiled tubing is again coiled around the holder in multiple turns.

Each column design has a specific advantage for performing the particular type of separation. The tubing 76 and tubing 78 are particularly suitable for performing extraction and high-speed countercurrent chromatography on a preparative scale. The column designs 82 and 84 are efficiently used for small-scale separations with a narrow-bore column.

In each separation, the column 42 is first filled with the stationary phase followed by sample injection through the sample port located at the outlet of the pump. Then, the apparatus is rotated at the desired revolutional speed while the mobile phase is introduced into the column 42 in the proper direction. The effluent from the outlet of the column 42 is monitored through an ultraviolet monitor and fractionated into test tubes with a fraction collector. After the separation is completed, the apparatus is stopped and the column contents are collected by connecting the inlet of the column to a pressured $N_2$ line. The column 42 is then flushed with a proper solvent such as methanol and dried by passing $N_2$ for several minutes before starting the next run.

What is claimed is:

1. An apparatus for countercurrent chromatography and particle separation comprising: a separation column means wound about a column holder; said holder being mounted on a rotary frame for rotating about its central longitudinal axis while simultaneously revolving around a vertical axis at the same angular velocity and in the same direction; said holder being inclined at an angle significantly greater than 0° and significantly less than 90° from said vertical axis; said tubing being fed to and returned from said column holder.

2. The apparatus of claim 1, further comprising means for rotating said inclined holder around said central longitudinal axis at one angular velocity in one direction and means for rotating said inclined holder around said central longitudinal axis at said one angular velocity in said one direction.

3. The apparatus of claim 1, wherein said tubing is placed parallel to said central longitudinal axis around said holder.

4. The apparatus of claim 1, wherein said tubing is coaxially wound around said holder.

5. The apparatus of claim 1, wherein said tubing is accommodated on said holder by forming multiple layers coaxially wrapped around said holder.

6. The apparatus of claim 1, wherein said column means comprises helically coiled tubing, portions of said helically coiled tubing being orientated parallel to said central longitudinal axis and placed about an outer periphery of said holder, said parallel portions being connected to adjacent parallel portions by a portion extending perpendicular to said longitudinal axis.

7. The apparatus of claim 1, wherein said column means comprises a helically coiled tubing, said helically coiled tubing being coaxially wrapped around an outer periphery of said column holder.

8. The apparatus of claim 1, wherein said holder is inclined from said vertical axis at an angle of about 1°–85°.

9. In an elution centrifuge comprising:
centrifugation means having an main axis, a separation column mounted on said centrifugation means, said separation column having an axis which is different from the main axis of revolution of said centrifugation means, a feed tube for introuducing fluids to said separation column, a return tube for discharging fluids from said separation column, said centrifugation means including means for revolving said separation column about the main axis of revolution of said centrifugation means and for simultaneously rotating said separation column about its axis at the same angular velocity and in a same direction, the improvement wherein said axis of said separation column is inclined from said main axis of revolution at an angle significantly greater than 0° and significantly less than 90°.

10. The device of claim 9, wherein said axis of said separation column is inclined from said main axis of revolution at an angle of about 1°–85°.

11. A device in accordance with claim 9 wherein said separation column comprises a helically coiled tube, said feed tube and said return tube being connected to the ends of said helically coiled tube.

12. A device in accordance with claim 9 wherein said centrifugation means comprises a vertical drive shaft at said axis of revolution, a tube holder for supporting said separation column, means for connecting said tube holder to said drive shaft and for maintaining said tube holder at a predetermined distance from said drive shaft and permitting said tube holder to rotate freely on its own axis, a first gear concentric with said drive shaft and mounted thereabout in fixed position, and a second identical gear fixedly connected about said tube holder.

13. A device according to claim 9 wherein said column has two ends, said feed tube introducing fluids into one end and said return tube discharging fluids from said other end.

14. A method of carrying out countercurrent chromatography in an elution centrifuge having a separation column and a feed tube for introducing fluids to the separation column, the method comprising:
filling said separation column through said feed tube with a first solvent, said separation column having an axis of rotation significantly inclined from a vertical axis at an angle of significantly less than 90°;
centrifuging said filled separation column by revolving said filled separation column about said vertical axis, while simultaneously rotating said separation column about its own inclined axis, the angular velocity of revolution and the angular velocity of rotation being equal and in a same direction, whereupon said centrifuging causes, within said separation column, essentially asymmetric distribution of radial force vectors and the development of substantial force vectors directed along and parallel to said axis of said separation column;
introducing a sample to be separated into the moving separation column;
pumping a second solvent, immiscible with said first solvent, into the moving separation column; and
recovering the separated fraction leaving the separation column.

15. The method of claim 14, wherein said axis of said separation column is inclined at an angle of about 1°–85° from the vertical axis.

* * * * *